(12) United States Patent
Chao

(10) Patent No.: US 11,000,621 B2
(45) Date of Patent: May 11, 2021

(54) SIPHON TYPE ESSENCE DIFFUSER HAVING BLOCK-PREVENTING AND LEAKAGE-PREVENTING CAPABILITIES

(71) Applicant: Majestic—M&A International Co., Ltd., Taipei (TW)

(72) Inventor: Hsuan-Yu Chao, Taipei (TW)

(73) Assignee: MAJESTIC-M&A INTERNATIONAL CO., LTD., Taipei (TW)

( * ) Notice: Subject to any disclaimer, the term of this patent is extended or adjusted under 35 U.S.C. 154(b) by 216 days.

(21) Appl. No.: 16/284,904

(22) Filed: Feb. 25, 2019

(65) Prior Publication Data

US 2020/0268926 A1    Aug. 27, 2020

(51) Int. Cl.
*A61L 9/14* (2006.01)
*A61M 11/00* (2006.01)
*B05B 17/06* (2006.01)

(52) U.S. Cl.
CPC .............. *A61L 9/14* (2013.01); *A61M 11/005* (2013.01); *B05B 17/0684* (2013.01); *A61L 2209/111* (2013.01); *A61L 2209/132* (2013.01); *A61M 2205/8206* (2013.01)

(58) Field of Classification Search
CPC .. A61L 9/14; A61L 2209/13; A61L 2209/133; A61L 2209/134; A61L 2209/111; A61L 2209/132; A61M 11/005; A61M 2205/8206; B05B 17/0684
USPC .................................................. 239/43–51.5
See application file for complete search history.

(56) References Cited

U.S. PATENT DOCUMENTS

| | | | | |
|---|---|---|---|---|
| 2,201,784 | A | * 5/1940 | Myers | A47K 17/00 239/41 |
| 3,864,080 | A | * 2/1975 | Valbona | A61L 9/14 422/4 |
| 5,238,187 | A | * 8/1993 | Zlotnik | A61L 9/127 222/187 |
| 8,668,115 | B2 | * 3/2014 | Sipinski | A61L 9/14 222/1 |
| 2008/0290186 | A1 | * 11/2008 | Zlotnik | A61L 9/127 239/43 |
| 2016/0107186 | A1 | * 4/2016 | Chao | A61L 9/00 239/102.2 |
| 2019/0283067 | A1 | * 9/2019 | Nanda | B05B 15/68 |

\* cited by examiner

*Primary Examiner* — Cody J Lieuwen
(74) *Attorney, Agent, or Firm* — Chun-Ming Shih; Best International Patents

(57) ABSTRACT

A siphon type essence diffuser having block-preventing and leakage-preventing capabilities includes an outer shell and a universal atomizer connector contained therein. The universal atomizer connector is of a tube shape formed integrally into a body, having a first end connectable to the bottle port of an essence oil container presently available on the market. A nozzle cover and an atomized plate are disposed on the tube port of the second end. An essence supply channel is disposed between the first end and the second end. A siphon essence oil supply mechanism is disposed on universal atomizer connector, with one end of a cotton rod pressing against a back side of the atomized plate, and with the other end of a cotton rod extending into the essence oil supply channel to absorb essence oil.

7 Claims, 11 Drawing Sheets

SIPHON TYPE ESSENCE DIFFUSER HAVING BLOCK-PREVENTING AND LEAKAGE-PREVENTING CAPABILITIES

BACKGROUND OF THE INVENTION

Field of the Invention

The present invention relates to the technology of ultrasonic atomizer, and in particular to a siphon type essence diffuser having block-preventing and leakage-preventing capabilities, to facilitate performing essence therapy.

The Prior Arts

In recent years, due to the rapid progress and development of the medical science and cosmetics industry, people are able to pay more attention to their medical health cares, and to keep a pleasing appearance. In this respect, ultrasonic aroma diffuser, beauty/health care device, water and essence mist humidifier, essence diffuser, etc. are utilized extensively in beauty shops and ordinary households, and that is realized by using the ultrasonic atomizing technology. As such, through the high frequency vibrations of the atomizing plate, the essence liquid in the container is atomized into minute particles of mist, for diffusing it into the surroundings.

The early design functions for the ordinary ultrasonic essence diffuser is rather insufficient. In application, the essence liquid in an essence oil container available on the market has to be dispensed into a specific container, then the specific container is installed on the essence diffuser to perform the essence atomizing function, thus causing quite inconvenience to a user. To overcome this deficiency, a new universal essence oil diffuser is proposed, for which an essence oil container presently available on the market can be screwed directly onto the universal atomizer connector of the main body in the universal essence oil diffuser for use, without the need to purchase other container articles or to perform other installation actions. This type of universal essence oil diffuser is easy to use, and an essence oil container can be screwed therein directly any time to perform essence therapy, Though this type of universal essence oil diffuser is easy to use, yet good air venting is lacking or the universal atomizer connector. Therefore, after continuous and repeated essence oil ejections, it tends to create negative pressure inside, to block passage of essence oil, and adversely affect smooth essence oil ejections. In addition, in order to save cost, the back of the atomizer plate is disposed directly to an end of the essence oil supply channel, and in-between, good leakage prevention is lacking. As such, its major drawback is that, the essence oil in a filled up container tends to leak directly from the atomizer plate.

Therefore, presently, the design and performance of essence oil diffuser is not quite satisfactory, and it leaves much to room for improvements.

SUMMARY OF THE INVENTION

In view of the problems and drawbacks of the prior art, the present invention provides a siphon type essence diffuser having block-preventing and leakage-preventing capabilities, comprising an outer shell and a universal atomizer connector contained therein.

Wherein, the universal atomizer connector is a tube piece formed integrally into a body, having a first end and an opposite second end. An essence oil supply channel is disposed between the first end and the second end, the diameter of the tube piece at the first end is greater than the diameter of the tube piece at the second end. An outer expansion ring is disposed on the tube port of the second end to connect and join an atomizer plate and a nozzle cover. From inside the tube piece at the first end is disposed inward in sequence a front connection port, an inner thread, and a rubber ring, to connect to a bottle port of an essence oil container available on the market, such that essence is transported from the first end to the second end.

On the universal atomizer connector is disposed a siphon essence oil supply mechanism, formed by a support sleeve tube and a cotton bar sleeved therein. One end of the cotton bar is pressed against a backside of the atomizer plate, and the other end of the cotton bar is extended inward into the essence oil supply channel to absorb essence oil.

A plug for preventing back leakage is disposed on the bottle port of the essence oil container, one end of the plug is a sleeve tube, and the other end of the plug is a cover plate, on which an outlet hole is extended inward, and a movable bead is disposed in the output hole. A push pin is disposed in the tube piece at the first end of the universal atomizer connector, to press against the movable bead to control essence oil output of the essence oil container.

In the present invention, a plurality of universal atomizer connectors can be put together into a body, to form a composite essence diffuser, so that a user may select and adjust among a plurality of essences to perform essence therapy effectively.

Compared with the existing technology of the Prior Art, the advantages of the siphon type essence diffuser having block-preventing and leakage-preventing capabilities are that, the overall design of the universal atomizer connector is improved to achieve effective leakage prevention, and essence oil can be supplied normally and smoothly without being blocked. In addition, the universal atomizer connector can be installed into the outer shell of various different shapes, so that it can be connected to the bottle port of an essence oil container presently available on the market, to eject atomized essences of various different flavors.

Further scope of the applicability of the present invention will become apparent from the detailed descriptions given hereinafter. However, it should be understood that the detailed descriptions and specific examples, while indicating preferred embodiments of the present invention, are given by way of illustration only, since various changes and modifications within the spirit and scope of the present invention will become apparent to those skilled in the art from the detailed descriptions.

BRIEF DESCRIPTION OF THE DRAWINGS

The related drawings in connection with the detailed descriptions of the present invention to be made later are described briefly as follows, in which.

DETAILED DESCRIPTION OF THE PREFERRED EMBODIMENT

The purpose, construction, features, functions and advantages of the present invention can be appreciated and understood more thoroughly through the following detailed descriptions with reference to the attached drawings.

Figure 1:
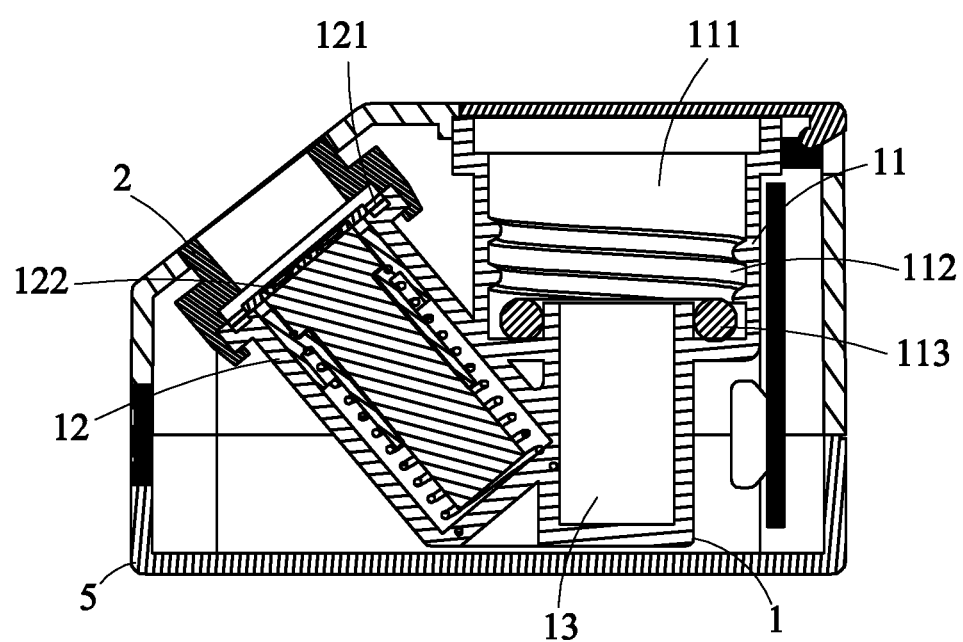
FIG. 1 is a cross section view of a siphon type essence diffuser having block-preventing and leakage-preventing capabilities according to the present invention.
Figure 2:
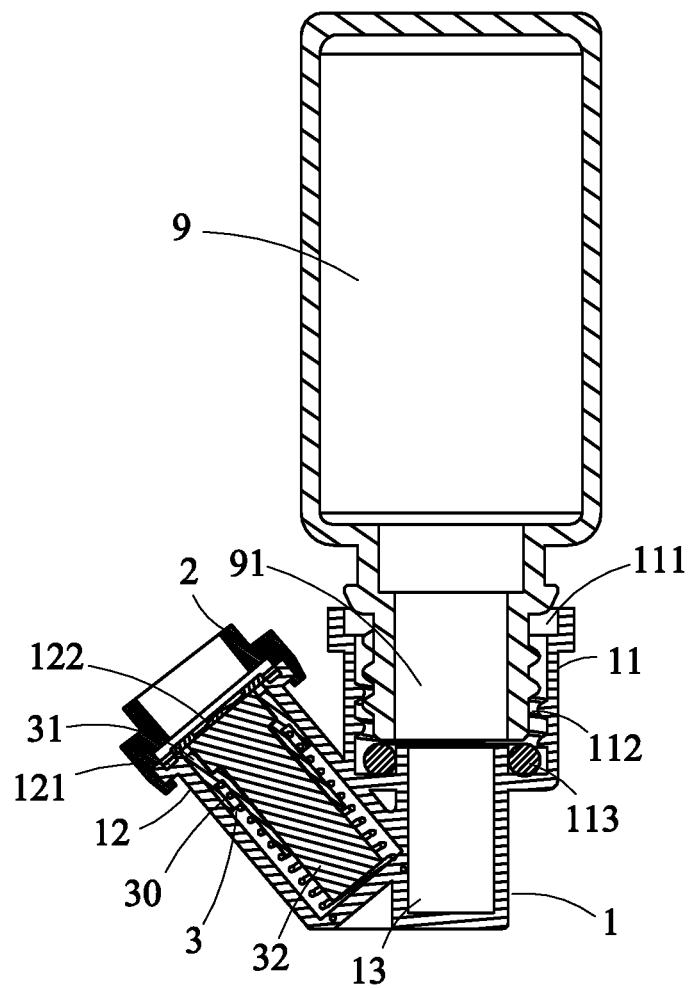
FIG. 2 is a cross section view of a universal atomizer connector according to the present invention.
Figure 3:
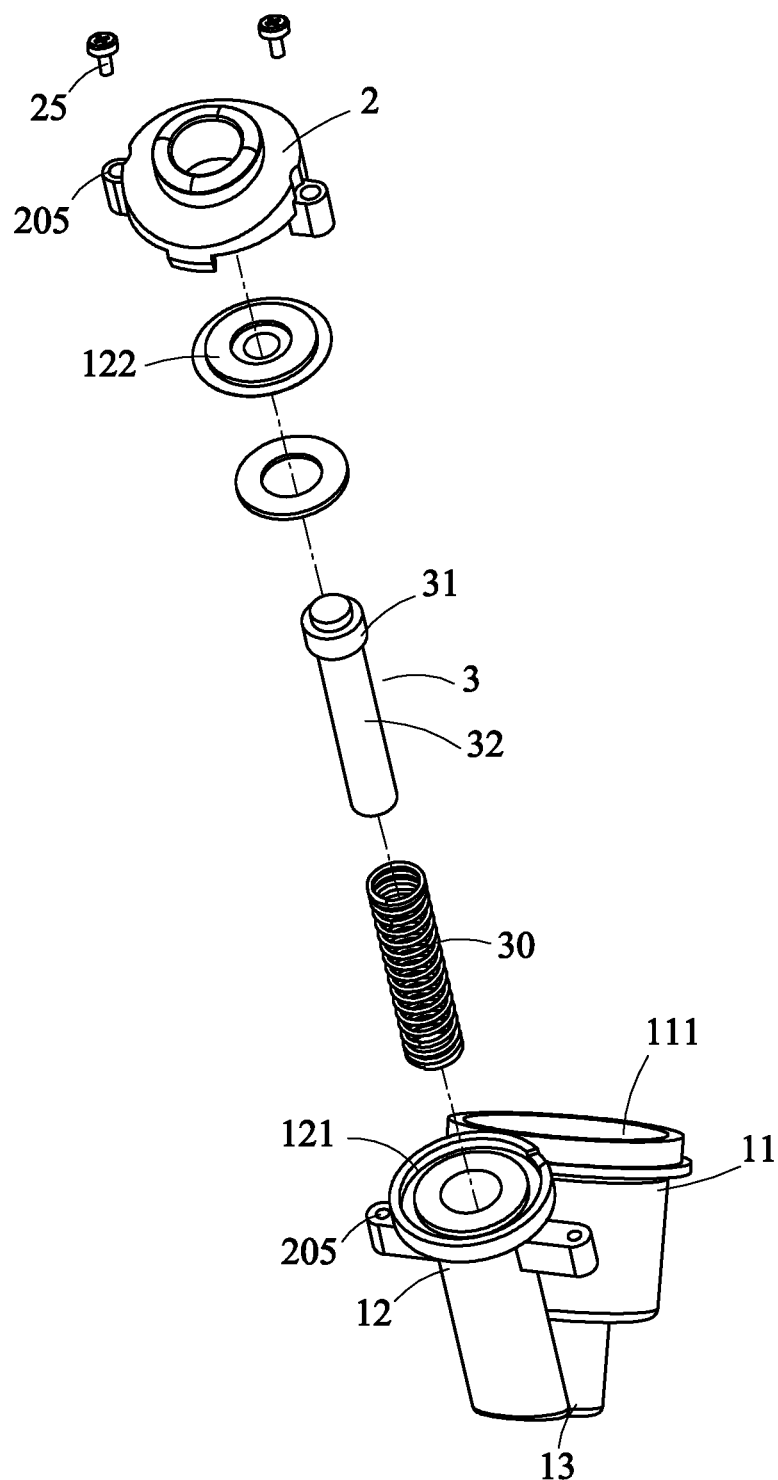
FIG. 3 is an exploded view of a universal atomizer connector according to the present invention.

Refer to FIGS. 1 to 3 respectively for a cross section view of a siphon type essence diffuser having block-preventing and leakage-preventing capabilities according to the present invention; a cross section view of a universal atomizer connector according to the present invention; and an exploded view of a universal atomizer connector according to the present invention. As shown in FIGS. 1 to 3, the present invention provides a siphon type essence diffuser having block-preventing and leakage-preventing capabilities includes an outer shell 5 and a universal atomizer connector 1 contained therein.

Wherein, the universal atomizer connector 5 is formed integrally into a tube piece, having a first end 11 and a second end 12 in opposite. An essence oil supply channel 13 is disposed between the first end 11 and the second end 12, The diameter of the tube port at the first end 11 is greater than the diameter of the tube port at the second end 12. An outer expansion ring 121 is disposed on the tube port of the second end 12 to connect and join an atomizer plate 122 and a nozzle cover 2. From inside the tube piece at the first end 11 is disposed inward in sequence a front connection port 111, an inner thread 112, and a rubber ring 113, to connect to a bottle opening 91 of an essence oil container 9 available on the market, such that essence in the essence oil container 9 is transported from the first end 11 to the second end 12.

On the universal atomizer connector 1 is disposed a siphon essence oil supply mechanism 3, formed by a support sleeve tube 31 and a cotton bar 32 sleeved therein. One end of the cotton bar 32 is pressed against a backside of the atomizer plate 122, and the other end of the cotton bar 32 is extended inward into the essence oil supply channel 13 to absorb essence oil.

Figure 4:
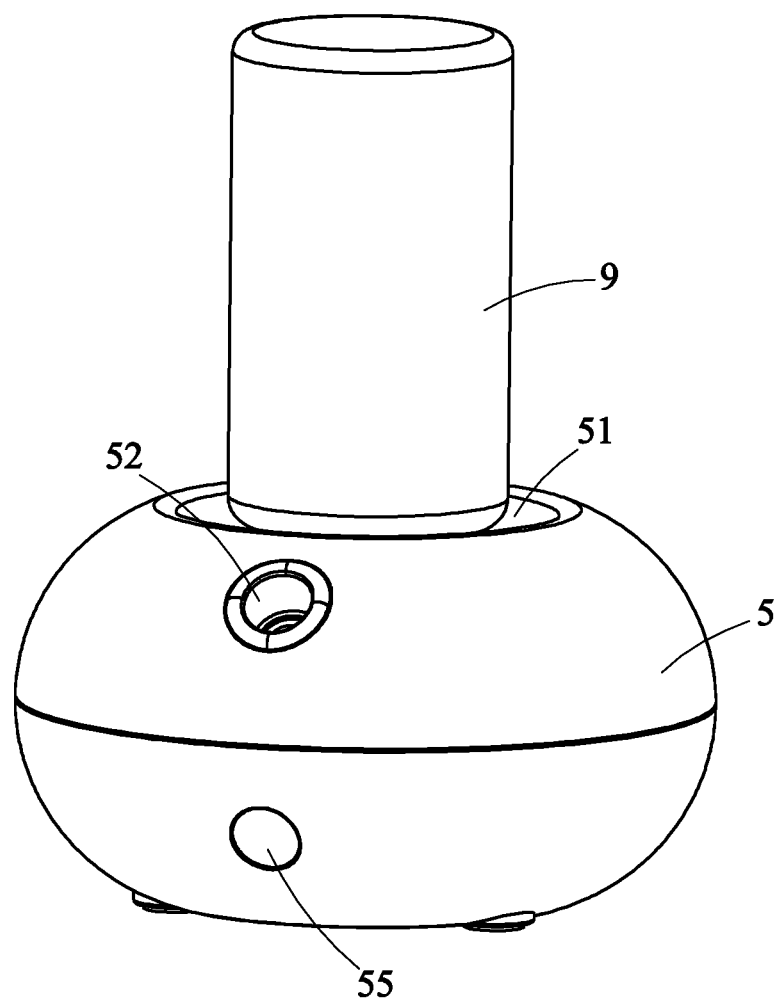
FIG. 4 is a schematic diagram of a siphon type essence diffuser having block-preventing and leakage-preventing capabilities in application according to the present invention.

As shown in FIGS. 3 to 4, the essence oil supply channel 13 is formed into a V shape having an angle, the support sleeve tube 31 is of a T shape, a spring 40 is disposed to sleeve around and press against a lower end of the support sleeve tube 31, with the other end of the spring 40 pressed against a bottom inner wall of the essence oil supply channel 13. As such, the cotton bar 32 is able to achieve a real tight connection with the back side of the atomizer plate 122, to ensure smooth essence oil supply and excellent atomized effect.

The nozzle cover 2 is provided with a protrusion hole plate, and at least two hole locking positions 205 are disposed respectively on two opposite sides of the nozzle cover 2, and respectively on two opposite sides of the outer expansion ring 121, for screws to lock and fix tightly, but the present invention is not limited to this.

In the present invention, since a siphon essence oil supply mechanism 3 is disposed on the universal atomizer connector 1, thus it is able to achieve leakage prevention, and block prevention to ensure smooth supply of essence oil.

The outer shell 5 is a of one of the following shapes: a cylindrical body, a column body, a circle body, a round block body, a block body, a spherical body, an elliptical sphere body, a polygon, and other geometric shapes. For example, the outer shell 5 can be of shapes as shown in FIGS. 4 to 8.

Figure 5:
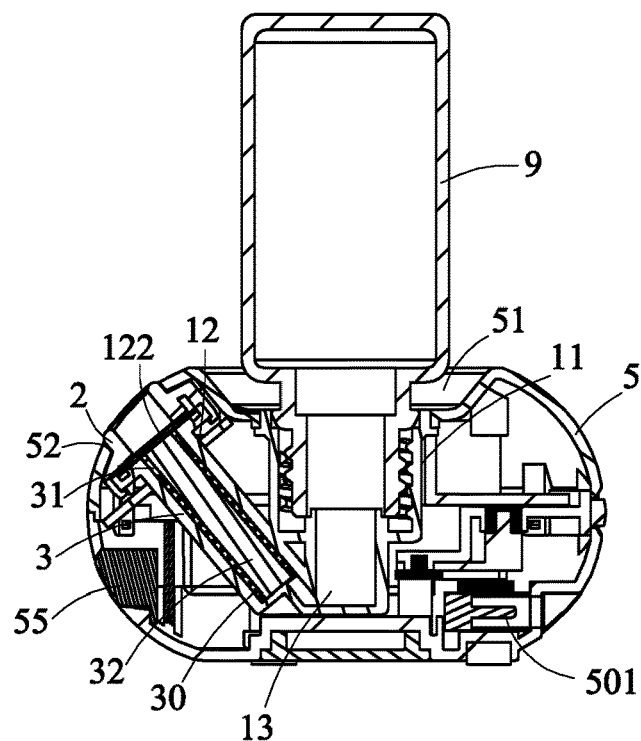
FIG. 5 is a cross section view of a siphon type essence diffuser having block-preventing and leakage-preventing capabilities in application according to the present invention.
Figure 6:
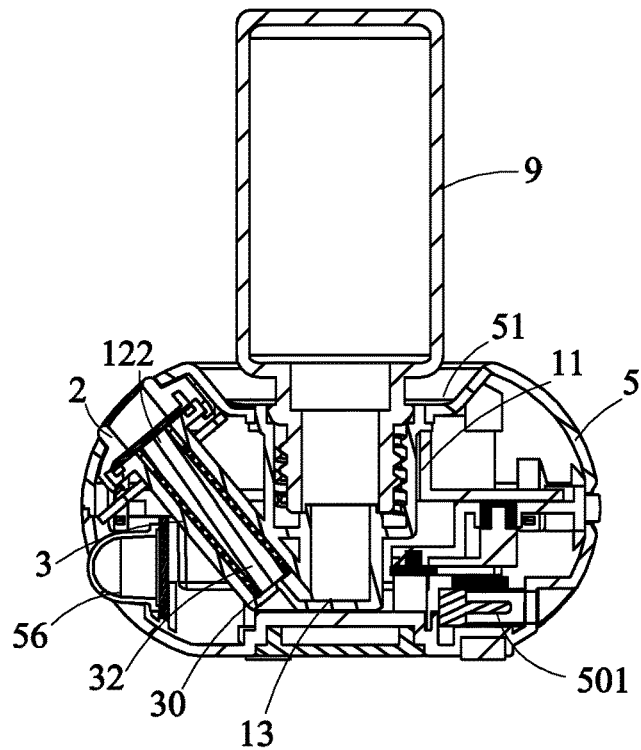
FIG. 6 is a cross section view of a sensor switch utilized in the present invention.

As shown in FIGS. 4 to 6, the outer shell 5 is adapted to receive and cover the universal atomizer connector 1, and the outer shell 5 further includes a circuit board 50 connected thereto, a placement port 51 disposed on the outer shell 5 corresponding to the first end 11 of the universal atomizer connector 1, an ejection port 52 is disposed on the nozzle cover 2 corresponding to the second end 12 of the universal atomizer connector 1, an operation switch 55 (as shown in FIG. 5) and a senor switch 56 (as shown in FIG. 6) are disposed on the outer shell 56, and both are connected to the circuit board 50, to control operations of the atomized plate 122.

Figure 7:
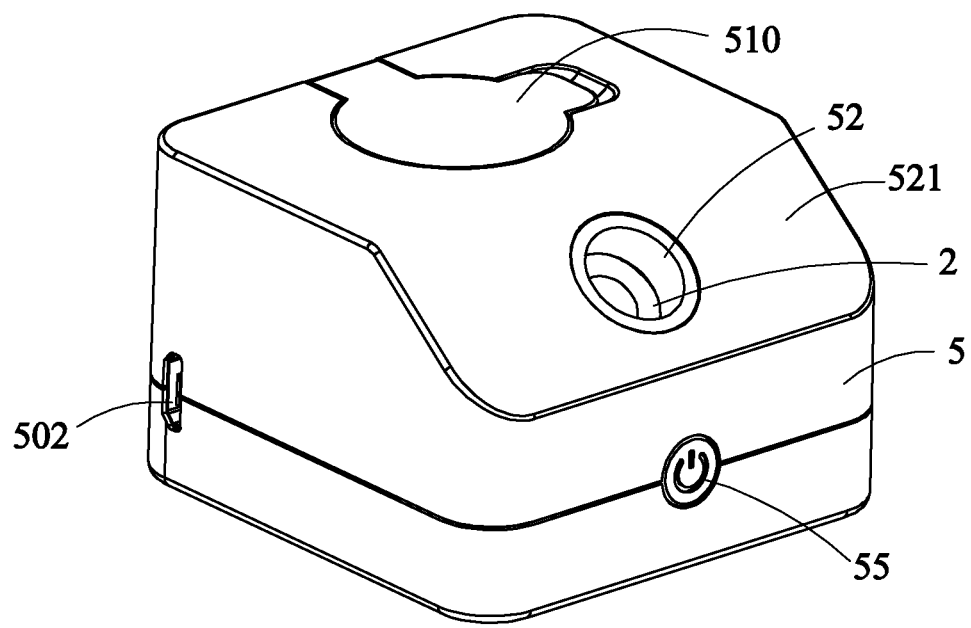
FIG. 7 is a schematic diagram of a siphon type essence diffuser having block-preventing and leakage-preventing capabilities in another application according to the present invention.
Figure 8:
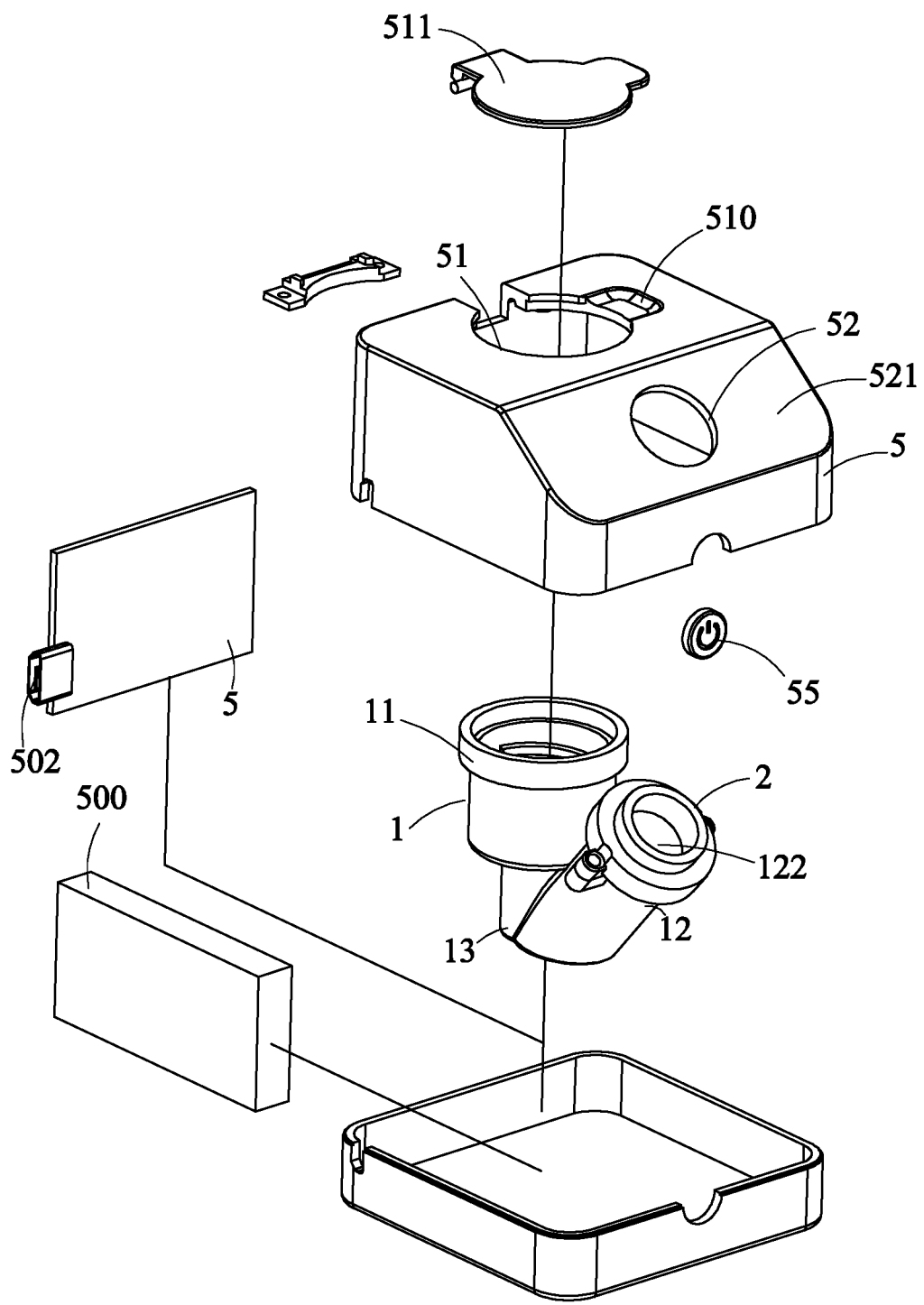
FIG. 8 is an exploded view of a siphon type essence diffuser having block-preventing and leakage-preventing capabilities in another application according to the present invention.

Refer to FIGS. 7 to 8 respectively for a schematic diagram of a siphon type essence diffuser having block-preventing and leakage-preventing capabilities in another application according to the present invention; and an exploded view of a siphon type essence diffuser having block-preventing and leakage-preventing capabilities in another application according to the present invention. As shown in FIGS. 7 and 8, a raise cover 511 is disposed on the placement port 51, an indent portion 510 is disposed beside the placement port 51, and a slant face 521 is disposed around the ejection port 52 of the outer shell 5 corresponding to the nozzle cover 2.

As shown in FIGS. 5 to 8, on the outer shell 5 is further disposed a DC power insertion hole 501 and a USB insertion hole 502, to provide DC power to a rechargeable battery 500 and the circuit board 50. In this way, the present invention can be placed on a fixed position, or can be carried while moving, to generate and provide atomized essence as required.

Figure 9:
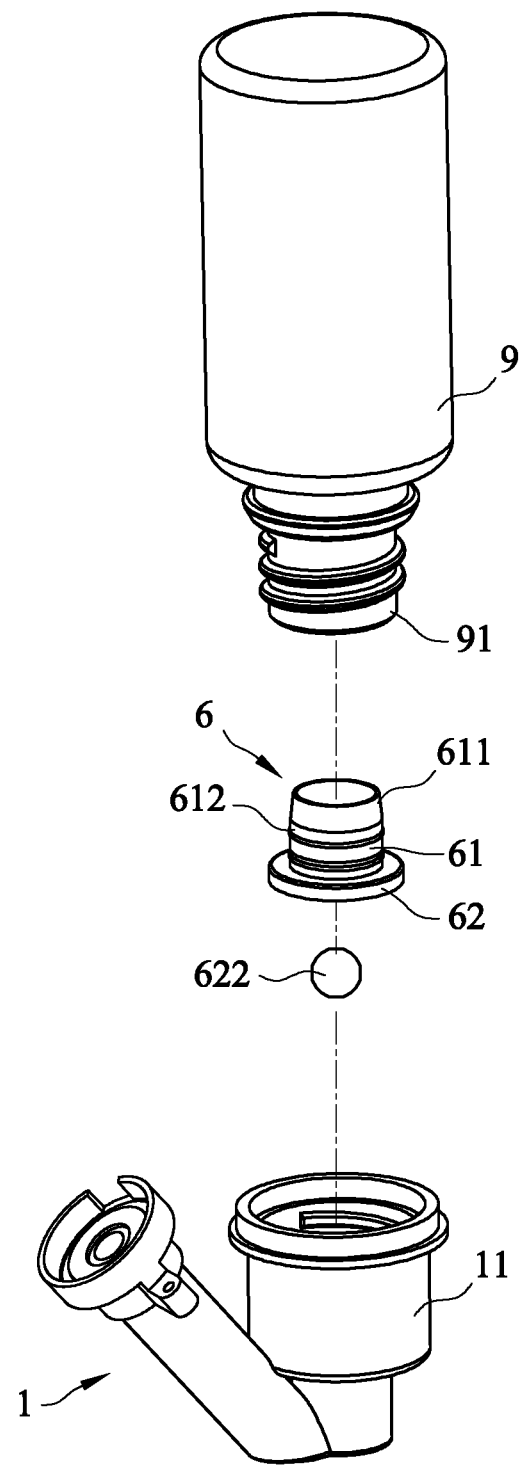
FIG. 9 is an exploded view of a back leak prevention plug installed on a bottle port of an essence oil container according to the present invention.
Figure 10:
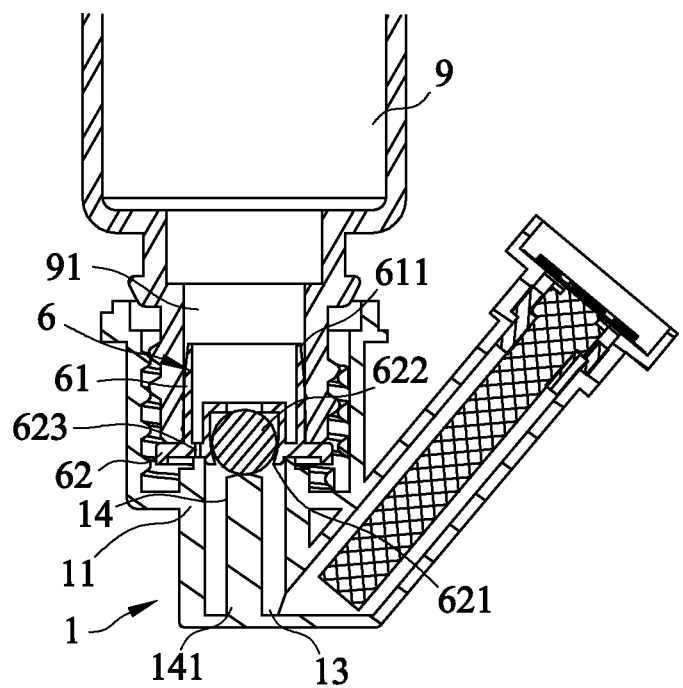
FIG. 10 is a cross section view of a back leak prevention plug installed on a bottle port of an essence oil container according to the present invention.

As shown in FIGS. 9 and 10, in the present invention, a plug 6 for preventing back leakage is disposed on the bottle port 91 of the essence oil container 9, on one end of the plug 6 is disposed a sleeve tube 61, and on the other end of the plug 6 is disposed a cover plate 62, on which an outlet hole 621 is disposed extending inward, and a movable bead 622 is disposed in the outlet hole 621. A small venting hole 623 is disposed beside the outlet hole 621 for the cover plate 62 of the plug 6, a tapering insertion guidance port 611 is disposed on the front end of the sleeve tube 61 of the plug 6, and a plurality of tight seal rings 612 are disposed and spaced apart on a side of the sleeve tube 61, to facilitate inserting the tapering insertion guidance port 611 into the bottle port 91 of the essence oil container 9, to prevent the essence oil from leaking out when the siphon type essence diffuser is put upside down.

Further, a push pin 14 is disposed in the tube port at the first end 11 of the universal atomizer connector 1, and in installation, to press against the movable bead 622 to control essence output of the essence oil container 9. In other words, when the push pin 14 is driven into the bottle port 91 to press against the movable bead 622, the essence oil in the essence oil container 9 is allowed to flow down. In contrast, when the push pin 14 pressing against the movable bead 622 is pulled out of the bottle port 91, the essence oil in the essence oil container 9 is not allowed to flow and leaked out, even when the siphon type essence diffuser is put upside down.

Figure 11:
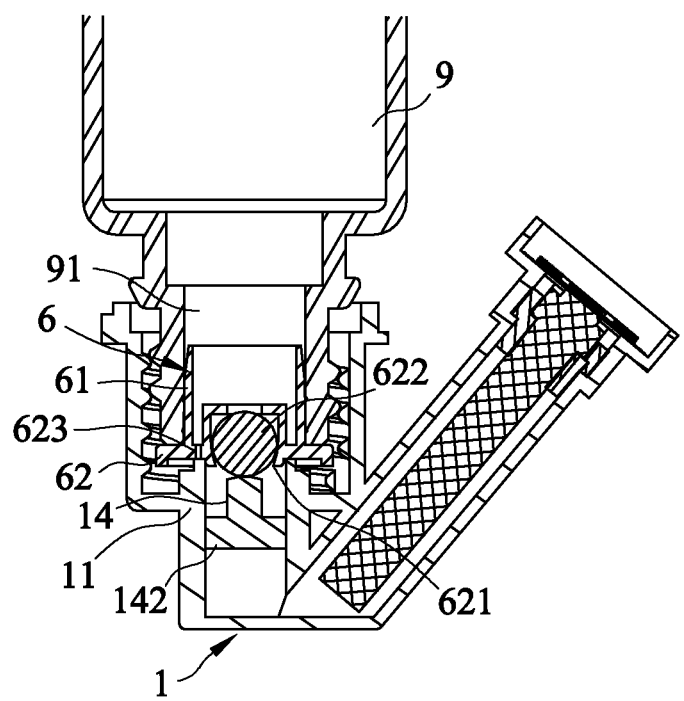
FIG. 11 is a cross section view of another back leak prevention plug installed on a bottle port of an essence oil container according to the present invention.

Then, as shown in FIGS. 10 and 11, the inner side end 141 of the push pin 14 is fixed at the inner bottom portion of the essence oil supply channel 13; or a connection rack 142 is disposed between a side of the push pin 14 and the tube port at the first end 11, but the present invention is not limited to this.

Figure 12:
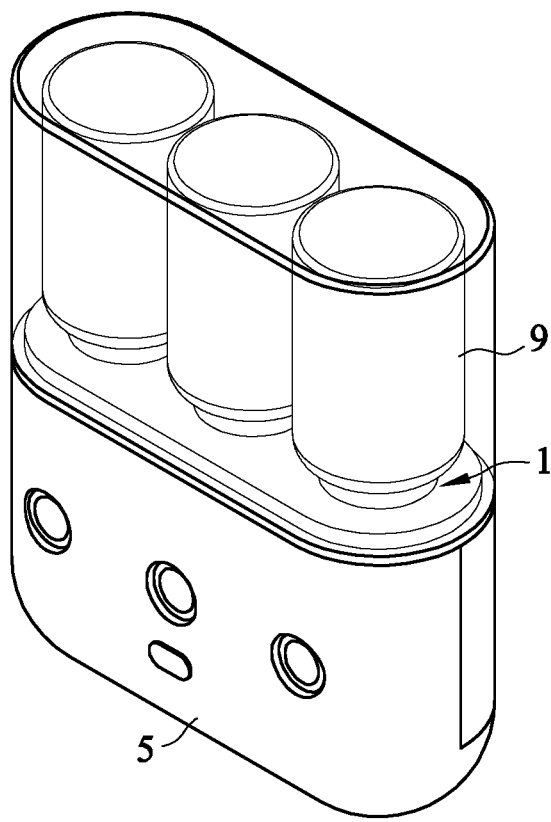
FIG. 12 is a schematic diagram of a siphon type essence diffuser having block-preventing and leakage-preventing capabilities in a vertical configuration according to the present invention.
Figure 13:
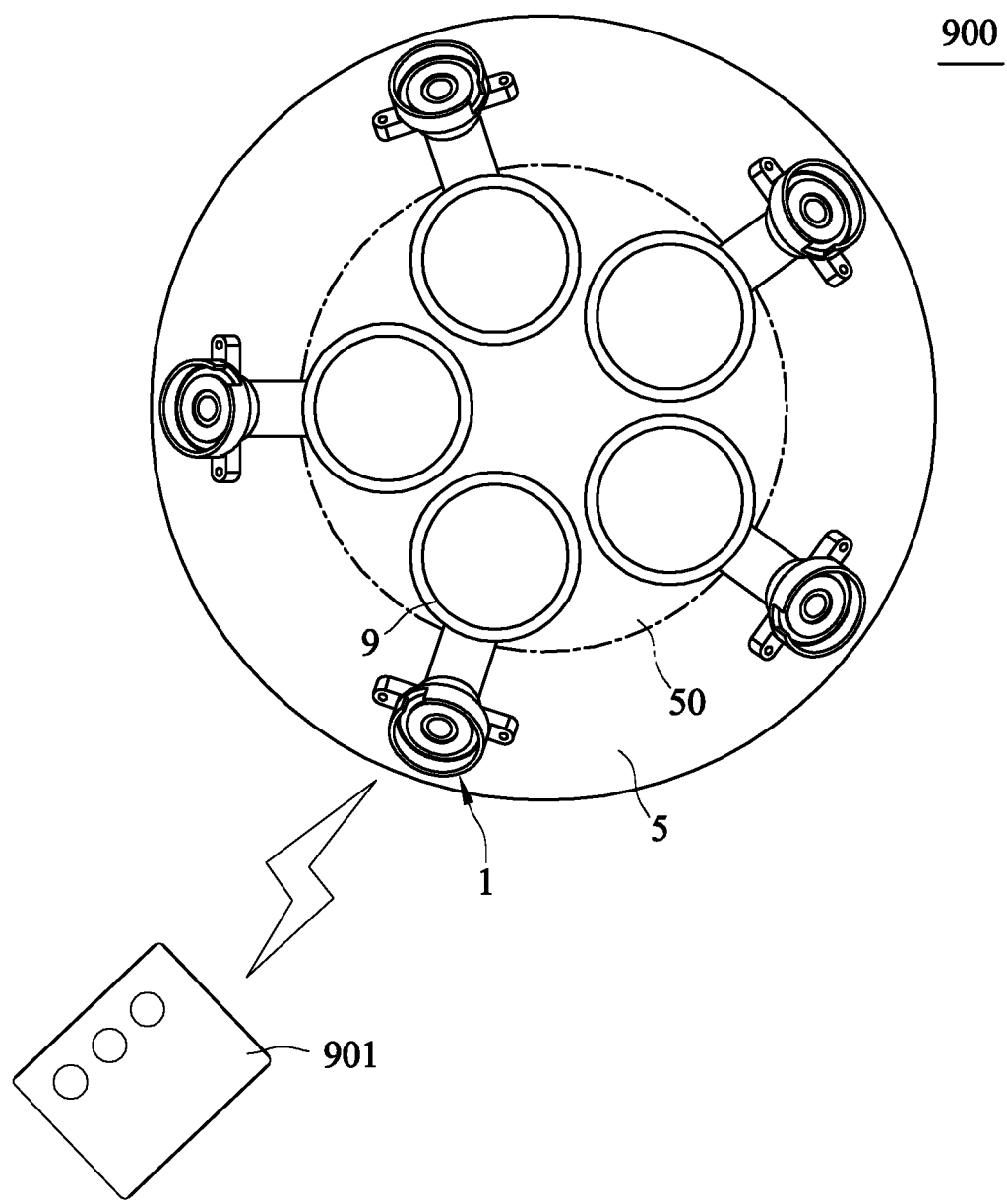
FIG. 13 is a schematic diagram of a siphon type essence diffuser having block-preventing and leakage-preventing capabilities in a circular configuration according to the present invention.

Finally, refer to FIGS. 12 and 13, a plurality of universal atomizer connectors 1 can be put together into a body, the number and configuration of the universal atomizer connectors 1 utilized are not limited. For example, in an embodiment of the present invention, two to six universal atomizer connectors 1 can be used to form into a line or a circle, to achieve a composite essence diffuser 900 capable of ejecting a plurality of essence flavors. Wherein, the respective atomizer plates 122 of the universal atomizer connectors 1 are connected to the circuit board 50. In addition, a remote controller 901 is disposed corresponding to the circuit board 50, such that a user may select and adjust among a plurality of essences to perform essence therapy effectively.

The above detailed description of the preferred embodiment is intended to describe more clearly the characteristics and spirit of the present invention. However, the preferred embodiments disclosed above are not intended to be any restrictions to the scope of the present invention. Conversely, its purpose is to include the various changes and equivalent arrangements which are within the scope of the appended claims.

What is claimed is:

1. A siphon type essence diffuser having block-preventing and leakage-preventing capabilities, comprising an outer shell, an atomizer plate, a nozzle cover, an essence oil container and a universal atomizer connector, contained therein, wherein the universal atomizer connector is formed integrally into a tube piece, having a first end and an opposite second end, an essence oil supply channel is disposed between the first end and the second end, a diameter of a tube port at the first end is greater than a diameter of the tube port at the second end, an outer expansion ring is disposed on the tube port of the second end to connect and join the atomizer plate and the nozzle cover, from inside the tube piece at the first end is disposed inward in sequence a front connection port, an inner thread, and a rubber ring, to connect to a bottle port of the essence oil container available on the market, such that essence is transported from the first end to the second end;

on the universal atomizer connector is disposed a siphon essence oil supply mechanism, formed by a support sleeve tube and a cotton bar sleeved therein, one end of the cotton bar is pressed against a backside of the atomizer plate, and the other end of the cotton bar is extended inward into the essence oil supply channel to absorb essence oil;

a plug for preventing back leakage is disposed on the bottle port of the essence oil container, on one end of the plug is disposed a sleeve tube, and on the other end of the plug is disposed a cover plate, on which an outlet hole extending inward, and a movable bead is disposed in the outlet hole; and a push pin is disposed in the tube port at the first end of the universal atomizer connector, to press against the movable bead to control essence oil output of the essence oil container, wherein the essence oil supply channel is formed into a V shape having an angle, so that the front connection port is extended upward, the support sleeve tube is of a T shape, a spring is disposed to sleeve around and press against a lower end of the support sleeve tube, with the other end of the spring pressed against a bottom of the essence oil supply channel.

2. The siphon type essence diffuser having block-preventing and leakage-preventing capabilities as claimed in claim 1, wherein the outer shell is one of the following shapes: a cylindrical body, a column body, a circle body, a round block body, a block body, a spherical body, an elliptical sphere body, and a polygon.

3. The siphon type essence diffuser having block-preventing and leakage-preventing capabilities as claimed in claim 1, wherein the nozzle cover is provided with a protrusion hole plate, and at least two hole locking positions are disposed respectively on two opposite sides of the nozzle cover, and respectively on two opposite sides of the outer expansion ring, for screws to lock and fix the nozzle cover to the outer expansion ring.

4. The siphon type essence diffuser having block-preventing and leakage-preventing capabilities as claimed in claim 1, wherein the outer shell is adapted to receive and cover the universal atomizer connector, and the outer shell further includes a circuit board connected thereto, a placement port is disposed on the outer shell corresponding to the first end of the universal atomizer connector, and an ejection port disposed on the nozzle cover corresponding to the second end of the universal atomizer connector, an operation switch and a sensor switch are disposed in the outer shell, and both are connected to the circuit board, to control operations of the atomizer plate.

5. The siphon type essence diffuser having block-preventing and leakage-preventing capabilities as claimed in claim 1, wherein on the outer shell is further disposed a DC power insertion hole and a USB insertion hole, to provide DC power to a rechargeable battery and the circuit board.

6. The siphon type essence diffuser having block-preventing and leakage-preventing capabilities as claimed in claim 1, wherein an inner side end of the push pin is fixed in a bottom portion of the essence oil supply channel.

7. A siphon type essence diffuser having block-preventing and leakage-preventing capabilities, comprising an outer shell, an atomizer plate, a nozzle cover, an essence oil container and a universal atomizer connector, contained therein, wherein the universal atomizer connector is formed integrally into a tube piece, having a first end and an opposite second end, an essence oil supply channel is disposed between the first end and the second end, a diameter of a tube port at the first end is greater than a diameter of the tube port at the second end, an outer expansion ring is disposed on the tube port of the second end to connect and join the atomizer plate and the nozzle cover, from inside the tube piece at the first end is disposed inward in sequence a front connection port, an inner thread, and a rubber ring, to connect to a bottle port of the essence oil container available on the market, such that essence is transported from the first end to the second end;

on the universal atomizer connector is disposed a siphon essence oil supply mechanism, formed by a support sleeve tube and a cotton bar sleeved therein, one end of the cotton bar is pressed against a backside of the atomizer plate, and the other end of the cotton bar is extended inward into the essence oil supply channel to absorb essence oil;

a plug for preventing back leakage is disposed on the bottle port of the essence oil container, on one end of the plug is disposed a sleeve tube, and on the other end of the plug is disposed a cover plate, on which an outlet hole extending inward, and a movable bead is disposed in the outlet hole; and a push pin is disposed in the tube port at the first end of the universal atomizer connector, to press against the movable bead to control essence oil output of the essence oil container, wherein a venting hole is disposed beside the outlet hole for the cover plate of the plug, a tapering insertion guidance port is disposed on a front end of the sleeve tube of the plug, and a plurality of rings are disposed and spaced apart on a side of the sleeve tube.

* * * * *